United States Patent [19]
Watterson

[11] Patent Number: 4,974,331
[45] Date of Patent: Dec. 4, 1990

[54] EXTENSIBLE GIRTH MEASURING DEVICE

[76] Inventor: Steven J. Watterson, 3355 Dew Point Ln., Sugarland, Tex. 77479

[21] Appl. No.: 422,530

[22] Filed: Oct. 17, 1989

[51] Int. Cl.⁵ ............................. G01B 3/10; G01B 5/08
[52] U.S. Cl. ...................................... 33/514.2; 33/2 R; 33/15; 33/561.3; 33/759; 128/774
[58] Field of Search ..................... 33/512, 561.1, 561.2, 33/561.3, 555.4, 2 R, 2 A, 2 H, 11, 15, 755, 759, 14, 16, 514.2; 128/774

[56] References Cited

U.S. PATENT DOCUMENTS

| | | | |
|---|---|---|---|
| 517,079 | 3/1894 | Veitch | 33/2 H |
| 1,935,998 | 11/1933 | Stradling | 33/15 |
| 2,129,582 | 9/1938 | Johansson | 33/555.4 |
| 2,691,221 | 10/1954 | Jobst | 33/15 |
| 3,327,394 | 6/1967 | Tenteris | 33/2 R |
| 3,832,780 | 9/1974 | Lewis | 33/2 R |
| 3,918,166 | 11/1975 | Mason | 33/512 |

FOREIGN PATENT DOCUMENTS

| | | | |
|---|---|---|---|
| 90566 | 5/1922 | Fed. Rep. of Germany | 33/15 |
| 885976 | 4/1958 | United Kingdom | 33/2 R |

*Primary Examiner*—Cuchlinski, Jr. William A.
*Assistant Examiner*—Alvin Wirthlin
*Attorney, Agent, or Firm*—Kenneth A. Roddy

[57] ABSTRACT

A girth measuring device for making simultaneous multiple measurements of the girth of an elongate portion of a body along its length has a generally rectangular base member adapted to be placed along the elongate portion of the body being measured and has index marks along one longitudinal side. A series of longitudinally spaced spring wound flexible measuring tapes on the base member extend and retract relative to the base member. A drawbar at the outer ends of the measuring tapes allow them to be simultaneously extended from their retracted position and placed in encircling relation about the body portion being measured. The drawbar is removably engaged on the base member to position the calibrations of the measuring tapes over the index marks. The girth measuring device allows measurements to be taken of each tape to determine the girth of the body portion being measured at longitudinally spaced locations along its length. One end of the base member may be configured to reside closely adjacent to a bone structure or joint adjacent to the body portion being measured whereby subsequent measurements are made at substantially the same longitudinally spaced locations. The spring tensioned measuring tapes firmly conform to the contour of the body portion being measured and subsequent measurements are consistently made with the same amount of tension.

11 Claims, 2 Drawing Sheets

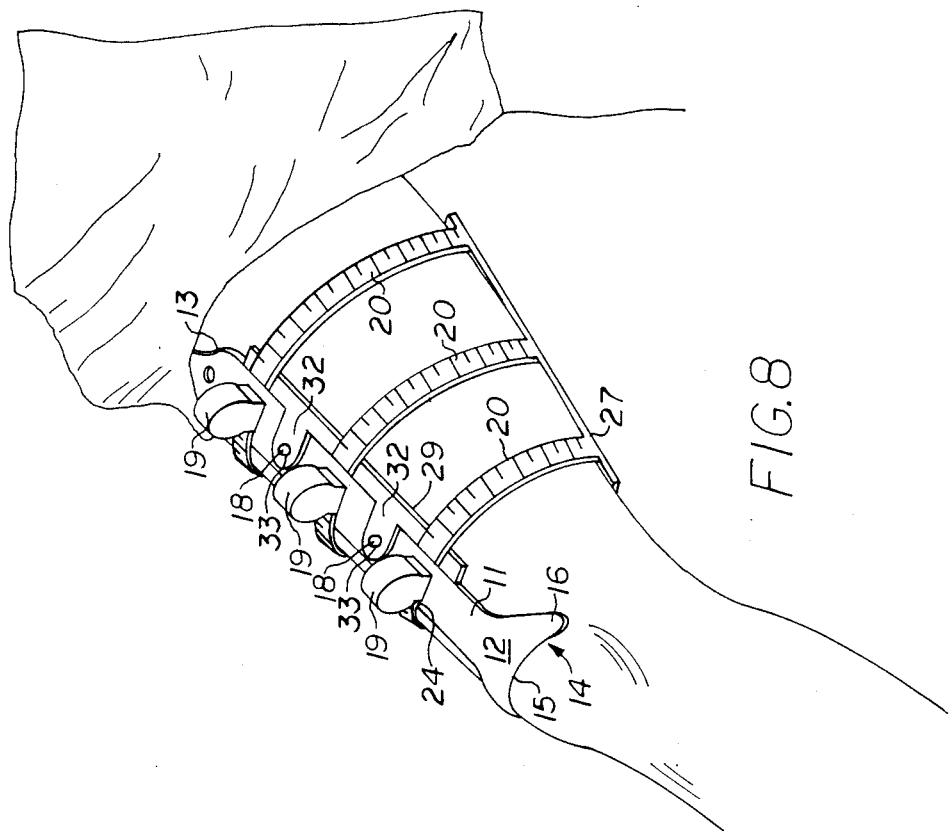
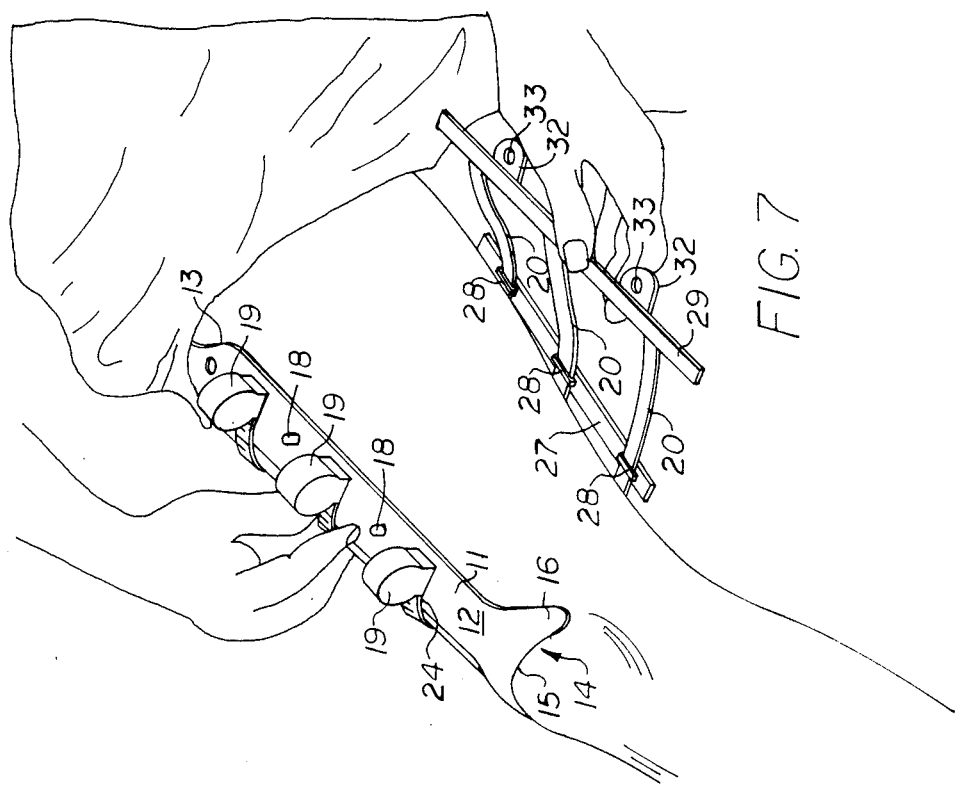

EXTENSIBLE GIRTH MEASURING DEVICE

BACKGROUND OF THE INVENTION

1. Field of the Invention

This invention relates generally to measuring apparatus, and more particularly to an extensible measuring apparatus for making multiple measurements of the girth of an elongate portion of a body along its length.

2. Brief Description of the Prior Art

Measuring devices for measuring the girth of an elongate portion of the body are known in the art. There are several patents which disclose girth measuring devices of various construction.

Beard, U.S. Pat. No. 48,644 discloses a measuring device to be used by clothing makers which comprises a net or frame of elastic cords combined with telescopically sliding tubular scales.

Pohle, U.S. Pat. No. 899,802 discloses a measuring device for dressmakers comprising an elaborate harness of vertical and horizontal inelastic measuring tapes which are wrapped about various portions of the body to take measurements.

Lewis, U.S. Pat. No. 3,832,780 discloses a body measuring apparatus for measuring and fitting surgical or therapeutic garments which utilizes a disposable sleeve of highly elastic material placed over the portion of the body to be fitted. A plurality of inelastic measuring tapes secured to the sleeve are each wrapped around the body portion and measurements are taken.

Jobst, U.S. Pat. No. 2,691,221 discloses a template for manufacturing individual body stockings which comprises an elongate blank of flexible non-elastic paper which is extended longitudinally on the body portion being measured and a series of spaced parallel strip portions extending outwardly therefrom which are wrapped around the body portion and secured to the longitudinal paper portion with adhesive to form a series of bands. The strips are then severed along a line parallel to the longitudinal portion to permit removal and the form is laid out on elastic stocking material to serve as a template for cutting the stocking material.

The present invention is distinguished over the prior art in general, and these patents in particular by a girth measuring device for making simultaneous multiple measurements of the girth of an elongate portion of a body along its length which has a generally rectangular base member adapted to be placed along the elongate portion of the body being measured and has index marks along one longitudinal side. A series of longitudinally spaced spring wound flexible measuring tapes on the base member extend and retract relative to the base member. A drawbar at the outer ends of the measuring tapes allow them to be simultaneously extended from their retracted position and placed in encircling relation about the body portion being measured. The drawbar is removably engaged on the base member to position the calibrations of the measuring tapes over the index marks. The girth measuring device allows measurements to be taken of each tape to determine the girth of the body portion being measured at longitudinally spaced locations along its length. One end of the base member may be configured to reside closely adjacent to a bone structure or joint adjacent to the body portion being measured whereby subsequent measurements are made at substantially the same longitudinally spaced locations. The spring tensioned measuring tapes firmly conform to the contour of the body portion being measured and subsequent measurements are consistently made with the same amount of tension.

SUMMARY OF THE INVENTION

It is therefore an object of the present invention to provide a girth measuring device for making simultaneous multiple measurements of the girth of an elongate portion of a body at longitudinally equally spaced locations along its length.

It is another object of this invention to provide a girth measuring device for making simultaneous multiple measurements of the girth of an elongate portion of a body which will eliminate the inaccuracies caused by wrapping a single tape around the body by hand multiple times.

Another object of this invention is to provide a girth measuring device for making repeated measurements of the girth of an elongate portion of a body at consistent longitudinally equally spaced locations along its length which will eliminate having to estimate the spacing of the locations from one measurement to the next.

Another object of this invention is to provide a girth measuring device which allows simultaneous multiple measurements to be made of the girth of an elongate portion of a body at longitudinally equally spaced locations along its length while allowing both hands to be free to record the readings.

Another object of this invention is to provide a spring tensioned girth measuring device for making simultaneous multiple measurements of the girth of an elongate portion of a body at longitudinally equally spaced locations along its length and at the same tension each time a measurement is made thereby eliminates the differences in measurements caused by the tightness or looseness of hand wrapping a single tape.

Another object of this invention is to provide a method for making simultaneous multiple measurements of the girth of an elongate portion of a body at longitudinally equally spaced locations along its length which simplifies the technique of morphological measurements and provides extremely accurate measurements.

Another object of this invention is to provide a girth measuring apparatus and method for making simultaneous multiple measurements of the girth of an elongate portion of a body at longitudinally equally spaced locations along its length which is particularly suited for taking comparative measurements such as comparing the muscle groups of one limb to the other limb for determining the growth or atrophy of a particular muscle over a length of time.

A further object of this invention is to provide a girth measuring apparatus and method for making simultaneous multiple measurements of the girth of an elongate portion of a body at longitudinally equally spaced locations along its length which provides extremely accurate measurements for making orthopedic braces and appliances.

A still further object of this invention is to provide a girth measuring apparatus for making simultaneous multiple measurements of the girth of an elongate portion of a body at longitudinally equally spaced locations along its length which is simple in construction, economical to manufacture, and rugged and reliable in use.

Other objects of the invention will become apparent from time to time throughout the specification and claims as hereinafter related.

The above noted objects and other objects of the invention are accomplished by a girth measuring device for making simultaneous multiple measurements of the girth of an elongate portion of a body along its length which has a generally rectangular base member adapted to be placed along the elongate portion of the body being measured and has index marks along one longitudinal side. A series of longitudinally spaced spring wound flexible measuring tapes on the base member extend and retract relative to the base member. A drawbar at the outer ends of the measuring tapes allow them to be simultaneously extended from their retracted position and placed in encircling relation about the body portion being measured. The drawbar is removably engaged on the base member to position the calibrations of the measuring tapes over the index marks. The girth measuring device allows measurements to be taken of each tape to determine the girth of the body portion being measured at longitudinally spaced locations along its length. One end of the base member may be configured to reside closely adjacent to a bone structure or joint adjacent to the body portion being measured whereby subsequent measurements are made at substantially the same longitudinally spaced locations. The spring tensioned measuring tapes firmly conform to the contour of the body portion being measured and subsequent measurements are consistently made with the same amount of tension.

BRIEF DESCRIPTION OF THE DRAWINGS

FIG. 7 is a perspective view of the girth measuring device being installed on a human thigh.

FIG. 8 is a perspective view of the girth measuring device after being installed on a human thigh and position for taking measurements.

DESCRIPTION OF THE PREFERRED EMBODIMENT

Figure 1:
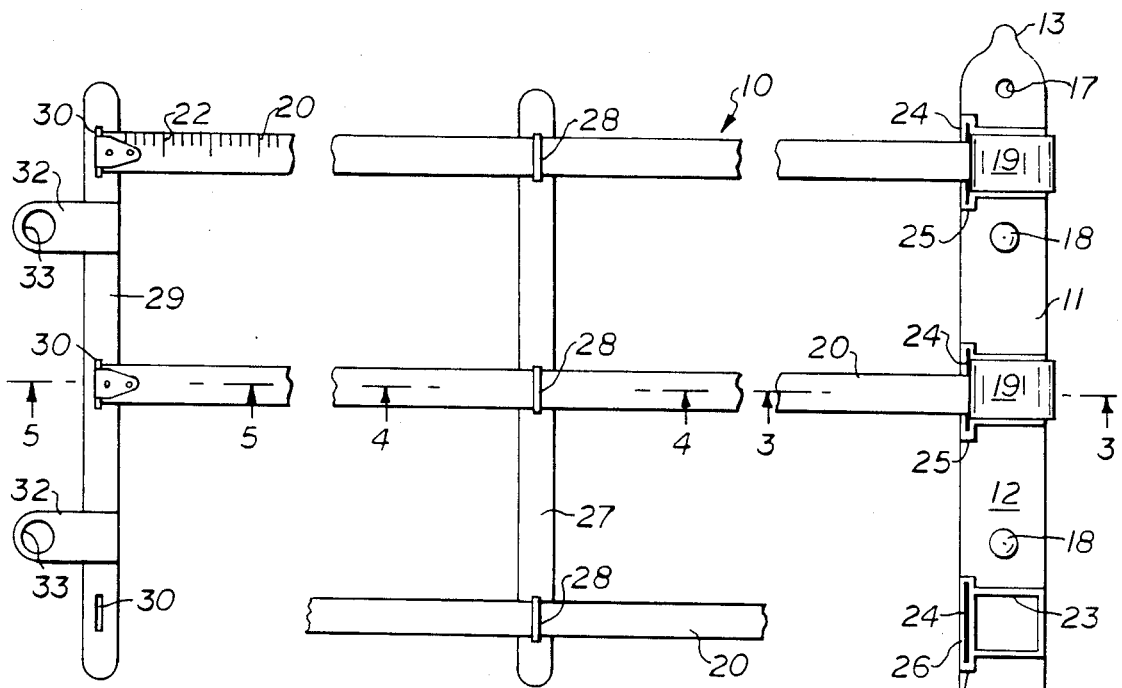
FIG. 1 is a top plan view of an extensible girth measuring device with portions of the measuring tape removed in certain places to more clearly show details of construction.
Figure 2:
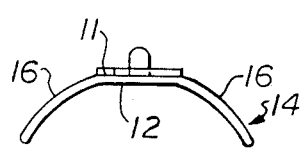
FIG. 2 is an end view of the measuring device of FIG. 1 taken along line 2—2.
Figure 6:
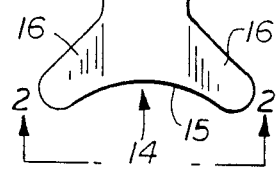
FIG. 6 is a cross section through the drawbar member received on the base member after the retractable measuring tape has been wrapped around the limb.
Figure 5:
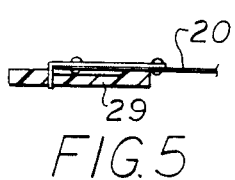
FIG. 5 is a cross section through the drawbar member taken along line 5—5 of FIG. 1 showing the end of the retractable measuring tape mounted thereon.
Figure 4:
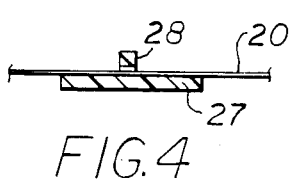
FIG. 4 is a cross section through the spacer bar taken along line 4—4 of FIG. 1 showing the spacer bar on the retractable measuring tape.

Referring to the drawings by numerals of reference, there is shown in FIG. 1, a preferred extensible girth measuring device 10. The measuring device 10 comprises a thin rectangular base member 11 having a longitudinal elongate flat portion 12 rounded at the top end 13 and a contoured laterally extending bottom end 14. As seen from the top (FIG. 1), the laterally extending bottom end 14 has an arcuate recess 15 transverse to the longitudinal axis. As seen from the end (FIG. 2), the sides, or wings 16 of the laterally extending bottom end 14 are curved downwardly relative to the longitudinal axis. The bottom end 14 serves as a contoured reference marker, as explained hereinafter. A small hole 17 extends through the flat portion 12 near the top end. A pair of longitudinally spaced rounded protrusions 18 extend upwardly from the top surface of the flat portion 12.

Figure 3:
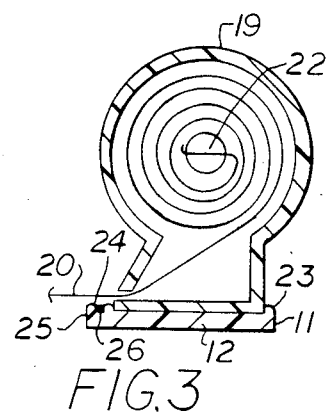
FIG. 3 is a cross section through the base member taken along line 3—3 of FIG. 1 showing a retractable measuring tape mounted thereon.

As seen in FIGS. 1 and 3, a series of retractable tape housings 19 are secured to the top surface of the flat portion 12 at longitudinally spaced locations and each contains a thin flexible measuring tape 20 marked with incremental calibrations 22 in inch or metric increments. One end of each tape 20 is secured within the housing 19 on a rotating spindle 22 and the tape 20 is wound thereon. The spring tensioned spindle 22 is spring tensioned by conventional means (not shown) to normally maintain the tape in a retracted (wound) condition.

A preferred method of securing the tape housings 19 to the base member 11 is to form a raised rectangular rim 23 on the top surface of the flat portion 12 in the molding operation to receive the bottom of the tape housing 19 and then secure the housings to the base by conventional means such as sonic welding or adhesives. This method allows precise positioning of the tapes relative to one another and to the arcuate recess 15.

A straight line 24 is provided on the top surface of the flat portion along the longitudinal edge adjacent the front of each of the tape housings 19 to provide an accurate sight index or "reading line" for reading the calibrations 22 on the tape 20. A preferred method of forming the reading lines 24 is to form a raised rectangular surface 25 on the top surface of the flat portion 12 in the molding operation which has a thin straight groove 26, then to fill the groove with a clearly visible colored material to form the line.

The tapes 20 are fed through a spacer bar 27. The spacer bar 27 is a flat rectangular bar which has raised loops 28 on its top surface which slidably receive the tapes 20. The longitudinal spacing of the loops 28 corresponds to the spacing of the tape housings 19 such that the tapes are always maintained parallel the same distance apart.

The terminal ends of the tapes 20 are secured to a drawbar 29. The drawbar 29 is a flat rectangular bar which has a series of longitudinally spaced slots 30 therethrough which receive the ends of the tapes 20. The spacing of the slots 30 correspond to the loops 28 of the spacer bar 27 and the tape housings 19 such that the tapes are always maintained parallel the same distance apart.

The drawbar 29 has a pair of longitudinally spaced extensions or tabs 32 which extend laterally outward from one side of the drawbar. The longitudinal spacing of the tabs 32 correspond to the spacing of the upwardly extending protrusions 18 on the top surface of the flat portion 12 of the base member 11. A hole 33 is provided near the ends of each tab 32 which is of sufficient size to be received on the protrusions 18.

In using a girth measuring device in accordance with the invention for measuring the human thigh, the following dimensions are recommended. The longitudinal elongate flat portion 12 from the rounded top end 13 to the apex of the arcuate recess 15 at the bottom end would be approximately 10¾" in length. The contour of the recess 15 and the downward curvature of the laterally extending wings 16 would be sufficient to be snugly received on and partially encompass the top of the kneecap (superior aspect of the patella).

Three tapes are recommended which should be spaced with the centerlines of the tape housings 19 mounted at 7.5 cm (3"), 15 cm (6"), and 23 cm (9") from the top of the patella (kneecap), or the apex of the arcuate recess 15.

The above described embodiment of the girth measuring device is suitable for use in measuring the muscle groups of the human thigh. However, it should be understood that other variations of the device may be provided for making multiple measurements of the girth of any limb or elongate portion of the body along its length without departing from the scope of the invention.

For example, the calf muscles may be measured by merely inverting the device. The bottom end of the base member may also be modified to fit other bone structures or joints, such as above or below the elbow for measuring the upper arm or forearm muscles, etc.

OPERATION

The following description is an example of how the girth measuring device would be used in measuring the muscle groups in the human thigh.

Prior to positioning the girth measuring device, the patient's limb should be clean and free of lotions, etc. If the patient has a shaved limb, it should be powdered. The limb should be in a relaxed supine position on a table or other flat surface with the knee slightly flexed.

Referring now to FIGS. 7 and 8, the base member 11 is held in one hand at the back or side of the thigh and the drawbar 29 is pulled outwardly therefrom with the other hand to extend the tapes 20 to approximately 24" or approximately 3" beyond what would be the expected maximum measurement.

The base member 11 is then placed on the top of the thigh with the recess 15 and the curved wings snugly received on and partially encompassing the top of the patella (kneecap) and the elongate flat portion 12 extending upwardly along center of the thigh (FIG. 7).

With the tapes 20 partially wrapped around the back of the thigh, the holes 33 in the drawbar tabs 32 are aligned with protrusions 18 and placed thereon. In this position, the longitudinal side of the drawbar 29 abuts the longitudinal side of the base member 11 and the spring tension on the tapes 20 maintains the device on the thigh.

The spacer bar 27 is slidably positioned to reside along the back of the thigh (FIG. 8). The thigh is then positioned to rest on the table or flat surface with the knee straight. At this point, the device should be checked to insure that it is positioned properly. Prior to taking the reading, and to insure an accurate measurement, it is recommended that the tapes 20 be pulled outwardly approximately 2" and allowed to gently self retract one at a time.

Then using the reading lines 24 to index the calibrations of the tape, readings are taken at all three reading lines to record measurements of the girth of the thigh at three locations along its length.

The girth measuring device allows three equally spaced measurements to be taken at one time and eliminates the inaccuracies caused by having to wrap a single tape around the thigh by hand three times and having to estimate the locations from one measurement to the next. The measurements are always spaced the same distance apart so that the exact location of the measurement is the same each time a measurement is made and the measurements can be made with both hands free to record the readings. The spring tension in the tapes provides the same firmness of the wrapped tapes each time a measurement is made thus, it eliminates the differences in measurements caused by the tightness or looseness of hand wrapping a single tape.

The girth measuring device greatly simplifies the technique of morphological measurements, and provides extremely accurate measurements. The device is particularly suited for taking comparative measurements. For example comparing the muscle groups of one thigh to the other thigh, and for determining the growth or atrophy of a particular muscle over a length of time.

The girth measuring device is also particularly useful in providing extremely accurate measurements which may be used for constructing and fitting orthopedic braces and appliances.

While this invention has been described fully and completely with special emphasis upon a preferred embodiment, it should be understood that within the scope of the appended claims the invention may be practiced otherwise than as specifically described herein.

I claim:

1. An apparatus for making multiple measurements of the girth of an elongate portion of a body along its length comprising:

a thin generally rectangular base member comprising a longitudinal elongate portion adapted to be received on the elongate portion of the body being measured and having index means along one longitudinal side, and having one end contoured to closely fit adjacent a bone structure or joint at one end of the elongate portion of the body being measured, longitudinally spaced flexible measuring strips on said base member adapted to extend and retract laterally relative thereto to be placed in encircling relation about the body portion being measured, each said measuring strip being calibrated on one side along its length in indicia of longitudinal dimension, and a drawbar member transversely secured to the laterally spaced free ends of said measuring strips for simultaneously extending said measuring strips from their retracted position and encircling said strips about said body portion being measured, said drawbar member adapted to be removably received on said base member to position said calibrations adjacent to said base member index means, whereby measurements may be taken along said index means of each said laterally spaced measuring strip to determine the girth of the body portion being measured at longitudinally spaced locations along its length, and the bone structure or joint adjacent which said base member contoured end is fitted serves as a reference point for the longitudinally spaced locations at which the girth measurements are taken such that subsequent measurements are made at substantially the same longitudinally spaced locations along the length of the body portion being measured.

2. An apparatus according to claim 1 including spacer means movably mounted on said measuring strips capable of being positioned intermediate said base member and said drawbar member for maintaining said measuring strips in laterally spaced relation, 3. An apparatus according to claim 2 wherein said spacer means comprises a thin rectangular bar slidably carried on said measuring strips in a transverse position relative thereto for maintaining said measuring strips in a parallel spaced relation.

4. An apparatus according to claim 1 wherein said rectangular base member elongate portion has a rounded top end and a contoured laterally extending bottom end,
said contoured laterally extending bottom end having an arcuate recess transverse to the longitudinal axis of said flat portion and the sides of the laterally extending bottom end curved downwardly relative to the longitudinal axis.

5. An apparatus according to claim 1 wherein each said flexible measuring strip is spring biased on said base member with equal tension to normally reside in its retracted position and is extended therefrom under spring tension, whereby
each said measuring strip firmly conforms to the contour of the portion of the body being measured at the longitudinally spaced locations, and
subsequent measurements are made with said measuring strips in encircling relation about said body portion at substantially the same tension.

6. An apparatus according to claim 5 wherein each said measuring strip comprises a flexible retractable tape member having one end wound on a spring tensioned spindle rotatably mounted within a housing which is secured on the top surface of said base member,
said spring tensioned spindle being spring tensioned to normally maintain said tape member in a retracted position.

7. An apparatus according to claim 1 wherein said index means comprises one or more straight lines on the top surface of said base member along one longitudinal edge over which said measuring strips are extended.

8. An apparatus according to claim 1 wherein said drawbar means comprises a thin rectangular bar secured to the free ends of said measuring strips in a transverse position relative thereto for maintaining said measuring strips in a parallel spaced relation.

9. An apparatus according to claim 1 wherein said rectangular base member and said drawbar means each have mutually cooperative engaging means thereon, whereby said drawbar is removably engaged on said base member to position said calibrations adjacent to said base member index means.

10. An apparatus according to claim 9 wherein said rectangular base member has a series of protrusions on its top surface, and
said drawbar means has a series of apertures which are removably received on said protrusions when said measuring strips are placed in encircling relation about said body portion being measured.

11. A method of making simultaneous multiple measurements of the girth of an elongate portion of a body along its length comprising the steps of:
providing a thin generally rectangular base member comprising a longitudinal elongate portion adapted to be received on the elongate portion of the body being measured, and having one end contoured to closely fit adjacent a bone structure or joint at one end of the elongate portion of the body being measured, and one or more index marks along one longitudinal side and a plurality of longitudinally spaced flexible measuring strips which simultaneously extend and retract laterally relative to the base member and each calibrated on one side along its length in indicia of longitudinal dimension,
placing the contoured end of said base member closely adjacent a bone structure or joint at one end of the elongate portion of the body to be measured and the longitudinal elongate portion of said base member on the elongate portion of the body to be measured,
simultaneously extending said measuring strips from their retracted position and encircling said strips about the elongate portion of the body to be measured,
simultaneously positioning said measuring strip calibrations on said one or more index marks, and
taking measurements along said one or more index marks of each said laterally spaced measuring strip to determine the girth of said body portion being measured at longitudinally spaced locations along its length relative to the bone structure or joint at which the contoured end of base member is placed whereby the bone structure or joint serves as a reference point for the longitudinally spaced locations at which the girth measurements are taken such that subsequent measurements are made at substantially the same longitudinally spaced locations along the length of the body portion being measured.

* * * * *